United States Patent [19]

Wegman

[11] Patent Number: 4,927,967
[45] Date of Patent: May 22, 1990

[54] PRODUCTION OF CARBOXYLIC ACIDS FROM ORGANIC FORMATE ESTERS USING RHODIUM COMPLEX CATALYSTS

[75] Inventor: Richard W. Wegman, South Charleston, W. Va.

[73] Assignee: Union Carbide Chemicals and Plastics Company Inc., Danbury, Conn.

[21] Appl. No.: 794,603

[22] Filed: Nov. 6, 1985

Related U.S. Application Data

[63] Continuation of Ser. No. 632,837, Jul. 20, 1984, abandoned.

[51] Int. Cl.$^5$ .................... C07C 51/353; C07C 53/08
[52] U.S. Cl. ................... 562/607; 260/405.6; 502/166; 560/265; 562/405; 562/490; 562/493; 562/496; 562/598; 562/606; 562/891
[58] Field of Search ............. 562/606, 607, 517, 497, 562/490, 493, 406, 496, 598, 517; 260/405.6, 413

[56] References Cited

U.S. PATENT DOCUMENTS

| | | | |
|---|---|---|---|
| 1,697,109 | 1/1929 | Dreyfus | 562/607 |
| 2,508,513 | 5/1950 | Groombridge | 562/607 |
| 3,060,233 | 10/1962 | Hohenschutz | 562/517 X |
| 3,769,329 | 10/1973 | Paulik et al. | 562/519 |
| 3,798,267 | 3/1974 | Wakmatsu et al. | 562/607 |
| 4,194,056 | 3/1980 | Antoniades | 562/516 |
| 4,212,989 | 7/1980 | Isshiki et al. | 560/232 |
| 4,374,278 | 2/1983 | Bryant et al. | 568/454 |
| 4,400,548 | 8/1983 | Abatjoglou et al. | 568/454 |
| 4,473,505 | 9/1984 | Mitchell, III | 260/439 |
| 4,491,675 | 1/1985 | Abatjoglou et al. | 568/454 |

FOREIGN PATENT DOCUMENTS

| | | | |
|---|---|---|---|
| WO80/01690 | 8/1980 | PCT Int'l Appl. | |
| 1286224 | 8/1972 | United Kingdom | 562/607 |
| 1326014 | 8/1973 | United Kingdom | 562/519 |

OTHER PUBLICATIONS

Bryant, F. J. et al., Amer. Chem. Soc., Petrochemicals Div. Pet. Chem., 18(1), Feb. 1973, pp. 193-195.
W. Heiber and R. Kummer, Chem. Ber., 100, pp. 148 to 159 (1967).
Applied Industrial Catalysis; vol. 1, Chapter 10, pp. 275 and 281, Academic Press, NYC (1983).

Primary Examiner—Vivian Garner
Attorney, Agent, or Firm—Reynold J. Finnegan

[57] ABSTRACT

A process for the production of organic carboxylic acids by the catalytic reaction of organic formate esters in contact with carbon monoxide and a homogeneous catalyst system of rhodium metal atom, a phosphorus containing ligand in which there is present at least one oxo oxygen atom attached to a phosphorus atom or a carbon atom to form a Z group and the

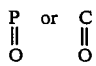

group in said Z group is located at least one carbon atom removed and preferably from 2-4 carbon atoms removed from the phosphorus atom of the molecules represented by the formulas

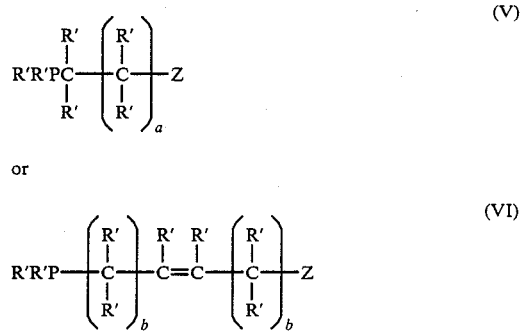

and a halogen source, under mild reaction conditions, wherein R' is H, aryl, alkaryl, aralkyl or alkyl, and wherein 1 or more of said R' groups can be substituted with a Z group but not more than 3 of said R' groups in the molecule are so substituted; a is an integer from 0–4; b is an integer from 0–3; and Z is P(O)R'R'; —C(O)OR" or C(O)R", wherein R" is R'.

19 Claims, No Drawings

PRODUCTION OF CARBOXYLIC ACIDS FROM ORGANIC FORMATE ESTERS USING RHODIUM COMPLEX CATALYSTS

This application is a continuation of prior U.S. application Ser. No. 632,837 filing Date Jul. 20, 1985.

BACKGROUND OF THE INVENTION

The production of organic compounds using synthesis gas, which is a mixture of carbon monoxide and hydrogen, or from carbon monoxide as one of the reactants has been known for a significant period of time. It is well known that one can produce methanol directly from synthesis gas and that methanol can be further reacted by hydroformylation, homologation and carbonylation reactions to produce acetaldehyde, ethanol and acetic acid or its methyl ester, respectively. It is also known that alcohols, esters, ethers, and other organic compounds can be reacted with synthesis gas or carbon monoxide to produce oxygenated organic compounds. The difficulties, however, have resided in the ability to carry out any one of these chosen reactions to produce the desired compound at acceptable efficiency, conversion rate and selectivity.

In almost all instances the reaction is generally catalyzed using a Group VIII transition metal compound as the catalyst and a halogen as the promoter. It is known that many other metal compounds and promoters can be used. In addition, the prior art has disclosed the use of secondary activators or ligands in conjunction with the metal catalysts and promoters. These secondary activators can be other metallic salts or compounds, amines, phosphorus compounds, as well as a multitude of other compounds that have been disclosed in the published literature. Thus, a typical catalyst system contains the metal atom catalyst, promoter and, optionally, ligands, solvents and secondary activators. Though a significant amount of literature does exist describing the production of carboxylic acids it is believed that it does not disclose or suggest the present invention. Several of the pertinent patents in this area are discussed below.

French Pat. No. 2,317,269, filed by Compagnie Des Metaux Precieux and published on Feb. 4, 1977, discloses the production of aliphatic carboxylic acids by the reaction of an alcohol with carbon monoxide in the presence of a catalyst containing at least three essential components, iridium atom, copper atom and halogen. This is not our process.

In European Patent Application No. 0018927; filed by Gauthier-Lafaye et al on Apr. 23, 1980 and published on Nov. 12, 1980, there is described a process for the production of monocarboxylic acids by the carbonylation of an alcohol using a nickel catalyst, a halide and a solvent. In this reference synthesis gas is used. In the instant process an organic acid is produced from an organic formate ester in the presence of carbon monoxide and a rhodium complex as the catalyst. No carbonylation is required in the instant process.

U.S. Pat. No. 3,060,233, issued to Hohenschutz on Oct. 23, 1962, discloses the carbonylation of methanol to acetic acid using a metal of the iron group of the Periodic Table and a halide. It does not disclose use of the instant rhodium complex at the mild pressure and temperature conditions employed herein.

U.S. Pat. No. 3,769,329, issued Oct. 30, 1973 to Paulik et al, discloses the use of a conventional rhodium catalyst and conventional ligands. The preferred mode of operation of this prior art process requires a large excess of water to ensure selectivity to acetic acid. This reference employs relatively extreme reaction conditions of temperature and pressure, and makes no distinction relating to the suitability of useful ligands. In addition, carbon monoxide is consumed which indicates a different kind of reaction than that of the instant invention.

U.S. Pat. No. 4,212,989, issued to Isshiki et al., on Jul. 15, 1980, describes a process for producing carboxylic acids or their esters by reacting an alcohol or an ether with carbon monoxide using a Group VIII metal catalyst and an iodine promoter. The reference contains no disclosure or suggestion of the production of carboxylic acids employing a specific rhodium complex under mild reaction conditions.

Another known procedure for producing acetic acid is the catalytic isomerization of methyl formate as shown by the reaction:

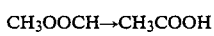

$$CH_3OOCH \rightarrow CH_3COOH$$

This procedure is shown in U.S. Pat. No. 1,697,109, issued to Henry Dreyfus on Jan. 1, 1929. The process described is a vapor phase isomerization reaction carried out at 200° C. to 450° C. at a pressure, for example, on the order of 200 atmospheres using a metal oxide or acetate catalyst. That is typical of the extreme reaction conditions normally used in this area of technology.

U.S. Pat. No. 2,508,513, assigned to Celanese Corporation and issued on May 23, 1950 claims a Group VIII metal atom based catalyst, e.g. nickel promoted with methyl iodide for the isomerization of methyl formate to acetic acid, carried out at 300° C. to 400° C. and at a pressure up to 6000 psig. Carbon monoxide may be present. It does not disclose the use of the rhodium complex catalyst of the present invention at low reaction temperature and pressure.

U.S. Pat. No. 3,798,267, issued Mar. 19, 1974, relates to the conversion of methyl formate to acetic acid in the presence of a catalyst system consisting essentially of activated carbon and a halogen promoter. The reference uses catalyst and starting materials different than those employed in the invention of this application.

U.S. Pat. No. 4,194,056, filed by Antoniades and issued Mar. 18, 1980, discloses the production of carboxylic acid from methyl formate using a soluble rhodium catalyst, halogen promoter and carbon monoxide. This is not the process of the instant invention, nor does this reference disclose or suggest the use of a specific rhodium complex nor the instant mild reaction conditions nor the instant LiI:CH$_3$I halogen source and the unexpected results achieved by their use.

British Patent Specification No. 1,286,224, issued Aug. 23, 1972 to Wakamatsu et al., relates to the reaction of methyl formate with carbon monoxide in contact with a rhodium catalyst and a halogen promoter to produce acetic acid. It contains no recognition of the distinct advantages achieved with the use of the instant specific rhodium complex nor of the instant mild reaction conditions.

British Patent Specification No. 1,293,193, issued Oct. 18, 1972 to Japan Gas-Chemical Company, Inc., relates to the direct conversion of formic acid esters to their corresponding carboxylic acids, in the presence of carbon monoxide, a catalyst that is a Group IIb or VIII metal and an organic polar solvent. It does not disclose use of the specific rhodium complexes of this invention nor of the mild operating conditions of the present process.

Japanese Patent Publication 50-16773, filed by Kuraishi et al and published on Jun. 16, 1975, discloses the production of an organic acid from the corresponding formic acid ester in the presence of carbon monoxide using a catalyst system containing cobalt, iron or mercury and a halogen plus an alkali metal salt of a lower aliphatic carboxylic acid, triamine or cyclic amine. The process is said to be carried out at high operating pressures.

Japanese Patent Publication No. 51-65703, filed by Mitsui Petrochemical and published on Jun. 7, 1976, discloses the reaction of methyl formate in the presence of carbon monoxide using a system containing a rhenium catalyst and halogen compound to produce some acetic acid. The principal product is methyl acetate. Acetic acid rates and selectivities are low.

Japanese Patent Publication No. 56-22745, filed by Wada et al., and published Mar. 3, 1981, discloses the isomerization of a formic acid ester to the corresponding acid in the presence of carbon monoxide, palladium atom, halogen and base. Acetic acid selectivity is low.

Japanese Patent Application No. 56-73040, filed by Isshiki et al., and published on Jun. 17, 1981, relates to a process for producing acetic acid by isomerizing methyl formate in the presence of carbon monoxide using a nickel catalyst, an iodine compound and an organic nitrogen compound.

Japanese Patent Application No. 56-83439, filed by Isshiki et al., and published Jul. 8, 1981, discloses a method for producing acetic acid by heating at elevated temperatures and pressures methyl formate and carbon monoxide in contact with a catalyst containing palladium, ruthenium and/or iridium metal atom and a halide promoter.

None of the previous five Japanese Patent Applications disclose a process for producing a carboxylic acid from an organic formate ester using a catalyst mixture which includes a rhodium complex, lithium iodide and methyl iodide.

European Patent Application No. 0045637, published Feb. 10, 1982 discloses converting formic acid esters to their corresponding carboxylic acids using a soluble iridium salt catalyst and an iodine promoter in the absence of an initial CO-pressure.

It can also be seen that the prior art contains many disclosures dealing with the catalytic production of acetic acid, including its production by isomerizing methyl formate. The art also discloses the production of other organic carboxylic acids from isomerization of other formate esters. One of the disadvantages of many of these reference processes is the presence of water with the eventual need to remove it from the desired product. This removal is both complicated and costly. Other disadvantages often include the simultaneous occurrence of other reactions leading to the formation of by-products, such as dimethyl acetal, ethanol, etc. These reactions compete with the organic acid production resulting in low conversion rate and selectivity to the desired organic acid-product.

Frequently, as shown above, typical prior art processes employing rhodium catalyst require rather harsh reaction conditions of temperature and pressure to obtain satisfactory yields of products. Such reaction conditions require use of expensive reactors, engender excessive energy costs, often lead to undesired by-products and cause excessive corrosion problems.

Many processes employed for producing organic acids use a catalyst system containing a source of metal atom and a source of halide atom. However, none of the references recognize the advantages of employing lithium iodide alone or admixed with methyl iodide in conjunction with a rhodium complex catalyst for efficient low temperature and pressure operations.

SUMMARY OF THE INVENTION

A process for the production of organic carboxylic acids has been discovered. The process can produce organic acids of the formula RCOOH, wherein R is a monovalent hydrocarbyl group, including an alkyl group having from 1 to 30 carbon atoms or aryl, aralkyl or alkaryl groups having from 6 to 10 ring carbon atoms with from 1 to 10 carbon atoms in the alk- moiety thereof or alkenyl having from 2 to 30 carbon atoms; and preferably an alkyl group having 1 carbon atom. The process includes the catalytic reaction of organic formate esters of the formula HCOOR in contact with carbon monoxide and a homogeneous catalyst system at mild reaction conditions.

The catalyst system consists essentially of rhodium metal atom, a halogen source and a phosphorus containing ligand in which there is present at least one oxo (=O) oxygen atom attached to a phosphorus atoms or a carbon atom to form a Z group and the

group in said Z group is located at least one carbon atom removed and preferably from 2-4 carbon atoms removed from the phosphorus atom of the molecules represented by the formulas

(V)

or

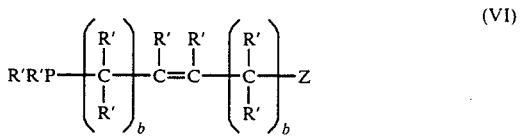

(VI)

wherein R' is hydrogen or unsubstituted or substituted (e.g. halogen, nitro, amino, etc.) aryl, aralkyl or alkaryl having from 6 to 10 ring carbon atoms and the alkyl moiety of the aralkyl or alkaryl group has from 1 to 10 carbon atoms and preferably 1 to 4 carbon atoms; or alkyl having from 1 to 10 carbon atoms and preferably 1 to 4 carbon atoms; and wherein 1 or more of said R' groups can be substituted with a Z group but not more than 3 of said R' groups in the molecule are so substituted; a is an integer from 0-4; b is an integer from 0-3; and Z is a member selected from the group consisting of

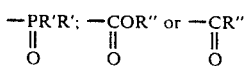

wherein R" is R'. R' can be the same or different.

The reaction conditions are mild, with the process being conducted usually at reaction temperatures less than about 170° C. and at reaction pressures less than about 450 psig.

The halogen source can be a single compound, such as lithium iodide, or a mixture of compounds as lithium iodide and methyl iodide.

Under catalytic conditions it is understood that a novel monocarbonyl rhodium complex of the formula A:

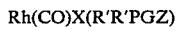

wherein X is halogen and R' and Z are as before, and wherein G represents the two

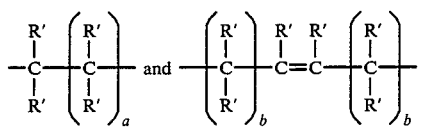

groups of formulas (V) and (VI), is formed in-situ.

The novel rhodium complex of the invention has been synthesized, isolated and characterized. The synthesized rhodium complex may be prepared in advance and used in place of the in-situ formed catalyst.

The Formula A rhodium complex is understood to be subject to the addition of a second mole of carbon monoxide to form a second catalytic dicarbonyl rhodium complex of Formula B and having the general formula:

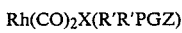

The Formula B rhodium complex can be prepared in advance of the process rather than being formed in-situ from Formula [A].

It has been found that the combination of the rhodium complex catalyst and halogen source provides high efficiency, high conversion rate and high selectivity never before achieved at such mild conditions.

DESCRIPTION OF THE INVENTION

In the catalytic reactions of synthesis gas or carbon monoxide in processes to produce oxygenated organic compounds there are several criteria required of the catalyst. The catalyst must be as stable as possible, it should have a high activity or conversion rate, and it should have as high a selectivity for the desired product as possible.

Stability of the catalyst relates to how long the catalyst remains functional before either breaking down or losing its catalytic effect.

Activity or conversion rate relates to the amount of reactants the catalyst converts to product per unit of time, generally expressed in g. mole per liter per hour (g mole/1/hr) or mole per hour (Mhr$^{-1}$).

Selectivity relates to the quantity of desired product produced, generally expressed in mole percent, based on the total amount of both desired products and undesired products produced.

The goal to be achieved is high values for all three criteria and continued efforts are being made to find new catalyst compositions to reach this goal without having a significant detrimental effect on the overall process. Toward this goal the prior art has developed catalyst systems containing a wide variety of metal atoms, promoters and activators, in many cases with diverse other components added. Though these catalyst systems are effective they usually require rather harsh reaction conditions and, accordingly, improvement is always desirable. Other factors having an impact on the process are the reaction temperature and reaction pressure. In the past it was generally thought necessary to increase these variables to improve overall selectivity and conversion.

The present invention is based on the unexpected and unpredictable discovery that the herein defined rhodium-catalyst systems which contain the specifically defined ligands produce carboxylic acids from formate esters at unexpectedly high efficiency, selectivity and conversion rates at mild reaction conditions. Optionally, a solvent and/or diluent as acetic acid can also be present.

In the process of our invention an organic formate ester is contacted with carbon monoxide in the presence of the inventive catalyst system. This system produces commerically desirable acids at unexpectedly high efficiency, conversion rate and selectivity, with a minimum of by-products and under mild reaction conditions. The overall reaction that occurs in the production of acids is theoretically:

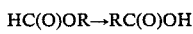

In the above formula R is a monovalent hydrocarbyl group. It can be an alkyl group having from 1 to 30 carbon atoms, preferably from 1 to 15 carbon atoms, and most preferably from 1 to 3 carbon atoms; an alkenyl group having from 2 to 30 carbon atoms, preferably from 2 to 15 carbon atoms and most preferably from 2 to 5 carbon atoms; or an aryl, aralkyl or alkaryl group having 6 or 10 ring carbon atoms, as phenyl and naphthyl, with from 1 to 10 carbon atoms, preferably 1 to 4 carbon atoms, in the alk-moiety thereof. The especially preferred R group is alkyl.

Examples of typical formic acid esters of the invention are methyl formate, ethyl formate, the propyl formates, the butyl formates, the decyl formates, 2-ethylhexyl formate, stearyl formate, phenyl formate, benzyl formate, vinyl formate, allyl formate, naphthyl formate, tolyl formate, mixtures thereof, and the like.

The R group can be linear or branched and it can be unsubstituted or substituted with groups which will not have an adverse effect on the reaction. The most preferred formates are the alkyl formates, including methyl formate, ethyl formate and the propyl formates with the especially preferred one being methyl formate.

The rhodium component of the catalyst system can be supplied from any number of sources, many of them are known to those of ordinary skill in the art. Thus, it is not necessary for an understanding thereof to specifically enumerate every suitable type and every specific compound since any of the known rhodium compounds can be used.

Most Group VIII transition metals, when employed with the halogen source will, at least to some small extent, catalyze the isomerization of methyl formate to acetic acid. This is particularly evident for Co, and Ir and the nickel triad of nickel, lead and platinum.

Accordingly, it may be possible to employ such metals, with the preferred rhodium metal component.

The essential rhodium component of the catalyst system of the present invention may be provided by introducing into the reaction zone a compound of rhodium or may be provided by introducing into the reaction zone, rhodium. Among the materials which may be charged to the reaction zone to provide the rhodium component of the catalyst system of the present invention are rhodium metal, rhodium salts and oxides, organo rhodium compounds, coordination compounds of rhodium, and the like. Specific examples of materials capable of providing the rhodium constituent of the catalyst system of the present invention may be taken from the following non-limiting partial list of suitable materials.

$RhCl_2$
$RhBr_3$
$RhI_2$
$RhCl_3 \cdot 3H_2O$
$RhBr_3 \cdot 3H_2O$
$Rh_2(CO)_4Cl_2$
$Rh_2(CO)_4Br_2$
$Rh_2(CO)_4I_2$
$Rh_2(CO)_8$
Rh metal
$Rh(NO_3)_3$
$[(n-C_4H_9)_4N][RH(CO)_2X_2]$ where X=Cl—, Br—, I—
$[(n-C_4H_9)_4As]_2[Rh(CO)_2Y_4]$ where X=Cl—, Br—, I—
$[(n-C_4H_9)_4P][Rh(CO)I_4]$
$Rh_2O_3$
$[Rh(C_3H_4)_2Cl]_2$
$K_4Rh_2Cl_2(SnCl_2)_4$
$K_4Rh_2Br_2(SnBr_3)_4$
$K_4Rh_2I_2(SnI_2)_4$ The rhodium metal atom concentration can vary over a wide range. Enough metal atom must be present to achieve reasonable reaction rates; however, an excess may, on occasion, result in undesired by-products formation. The mole ratio of rhodium atom to organic formate ester can vary from 1:25 to 1:20,000, the preferred range is from about 1:40 to 1:1000, with the most preferred range being from about 1:100 to 1:500. The amount used is not a critical feature in this invention and higher rhodium concentrations are acceptable but are influenced by economic considerations.

In general the rate of reaction increases with increasing rhodium concentration. For most purposes it is sufficient to employ a rhodium concentration from about 0.0001 to 1 mole per liter, preferable from about 0.01 to 0.1 mole per liter, although higher or lower concentrations may be utilized, depending, in part, upon economic considerations.

The second component of the catalyst system is a halogen source which contains a metal halide employed alone, or, more preferably, in combination with a halide promoter. The metal halide, which is a Group I, II, V, VI, or VIII metal halide must be present. A preferred metal halide is strontium halide. The most preferred metal halide is lithium halide.

The halide promoter component of the halogen source can be a halogen compound containing iodine, bromine or chlorine or two or more of the same, or the elemental halogen per se, or any mixtures of compounds and/or elements. Their identities are well known to those of ordinary skill in this art.

The preferred halide promoters are methyl iodide and iodine. As indicated, other suitable halogen compounds are well known to those of average skill in this art; thus a complete listing is not necessary for their comprehension.

The lithium halide can be charged directly to the process or it can be formed in-situ by any combination of lithium compound and halide component that will result in the formation of lithium halide during the reaction. Lithium bromide can also be used, but lithium iodide is the preferred lithium halide. Strontium iodide has also been found to be an effective, and, therefore, preferred, halogen source.

The presence of lithium iodide in conjunction with a halide promoter, such as methyl iodide, is a preferred embodiment of this invention. Direct charge of lithium iodide is the preferred form. However, any convenient combination of compounds for in-situ formation of lithium iodide can be used. This includes the use of lithium carboxylates, carbonates and the like with a halogen compound such as iodine or an alkyl halide. A suitable combination for in-situ formation is lithium formate (with the same functionality as the instant methyl formate ester feed-stock) and an alkyl halide.

Illustrative of suitable halogen sources thereof there can be mentioned barium iodide, hydriodic acid, cobalt iodide, potassium iodide, lithium iodide, sodium iodide, calcium iodide, ammonium iodide, methyl iodide, ethyl iodide, propyl iodide, 2-ethylhexyl iodide, n-decyl iodide, acetyl iodide, propionyl iodide; the organic ammonium iodides of the formula $R'''_4NI$ and the organic phosphonium iodides of the formula $R'''_4PI$ in which $R'''$ is alkyl, saturated or unsaturated, substituted or unsubstituted, having from 1 to about 10 carbon atoms or aryl, unsubstituted or substituted, having from 6 to 10 ring carbon atoms such as trimethyl ammonium iodide, tetraethyl ammonium iodide, tetra-2-ethylhexyl ammonium iodide, tetraphenyl ammonium iodide, tetramethyl phosphonium iodide, tetra-2-ethylhexyl phosphonium iodide, tetrapropyl phosphonium iodide, methyltriphenyl phosphonium iodide, and the like; methylammonium iodide, tri-p-tolyl-ammonium iodide, decylammonium iodide, ethylphosphonium iodide, triphenylphosphonium iodide, tricylcohexylphosphonium iodide, tri-p-tolyphosphonium iodide, and the like.

Also useful are bromine and its corresponding compounds and chlorine and its corresponding compounds. Any source of halogen atom can be used provided that it does not have a deleterious effect on the reaction.

The preferred halide promoters are methyl iodide and hydriodic acid, especially methyl iodide.

The amount of halogen source charged depends, in part, on the amount of rhodium employed. Sufficient halogen source must be present to exert a promoting effect on the reaction and to result in high efficiency, conversion rate and selectivity to the desired acid. Where the halogen source is a lithium halide, such as lithium iodide, solely, the mole ratio of LiX:Rh may vary widely. For the preferred LiI, the mole ratio of LiI:Rh ranges from 1:200 to 200:1 and, particularly, from 1:1 to 128:1. When the halogen source is a mixture of, for example, lithium iodide and methyl iodide, then the same LiI:Rh ratio is maintained, and the $CH_3I$:LiI mole ratio ranges from 1:200 to 200:1 and more preferably, from 10:1 to 1:10.

The third component of the catalyst system is a phosphorus-containing ligand of the formula R'R'PGZ, wherein R' and G are as prevously defined, and Z is selected from the group:

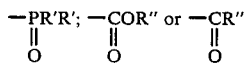

The R' aryl, aralkyl or alkaryl groups have from 6-10 ring carbon atoms. The alkyl moiety of the alkaryl or aralkyl group has from 1 to 10 carbon atoms, preferably 1 to 4 carbon atoms. The alkyl group has from 1 to 10 carbon atoms and preferably 1 to 4 carbon atoms.

In a first embodiment, the phosphorus-containing ligand has the general formula

 (I)

wherein R' and G are as before. The R' groups can be alike, different or mixed. Typical ligands of this embodiment include:

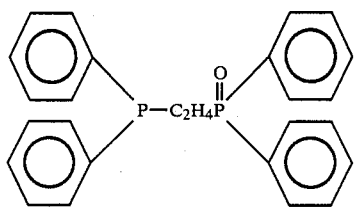 (1)

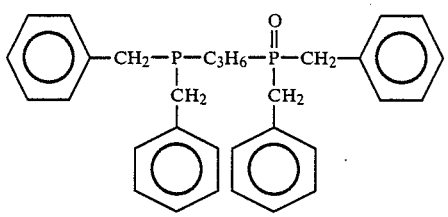 (2)

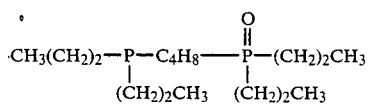 (3)

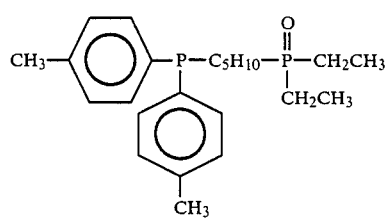 (4)

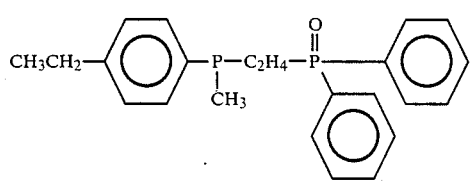 (5)

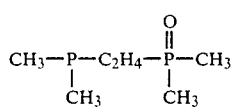 (6)

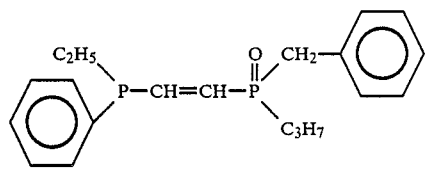 (7)

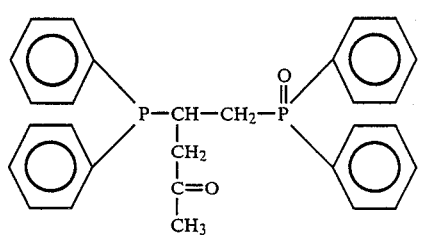 (8)

An especially preferred ligand of Formula (I) is

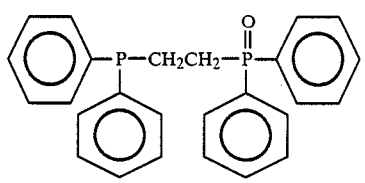

In a second embodiment the phosphorus-containing ligands have the general formula (II):

and in third embodiment the phosphorus-containing ligands have the general formula III:

wherein R' and G are as before; and R" is R'.

Typical examples of formula II compounds include:

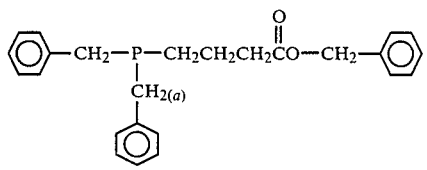 (a)

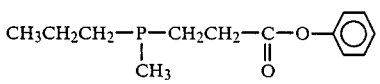 (b)

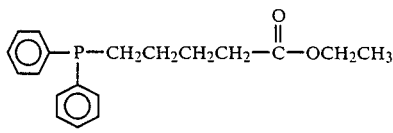 (c)

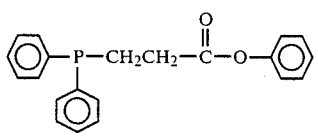 (d)

-continued

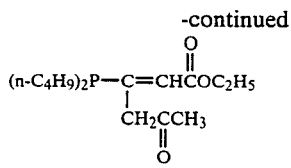 (e)

Typical examples of formula (III) compounds include:

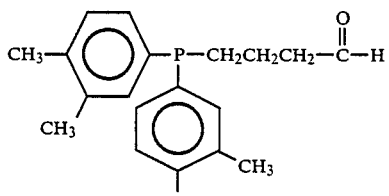 (f)

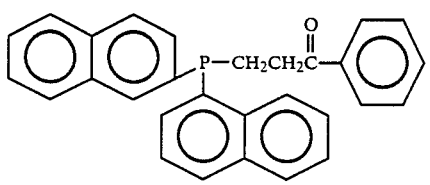 (g)

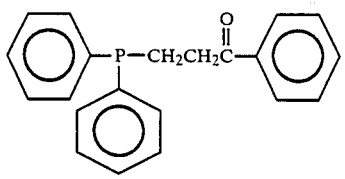 (h)

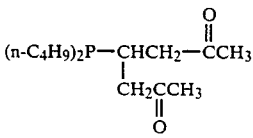 (i)

It has been found that conventional ligands such as $ER_3$ ($E=P, N, As$ and $R=$organic moiety) and chelating agents, such as $R'R'P(CH_2)_nPR'R'$ tend to deactivate the catalyst system at low temperature and pressure.

The reactive rhodium complex of formula A can be generally prepared and isolated by the typical reaction involving the dissolution of $[Rh(CO)_2Cl]_2$, or any other halide compound of this formula, in an inert solvent, such as dichloromethane, benzene, toluene and like, under inert atmospheric conditions. A stoichiometric amount of phosphine, based on the rhodium content, is added, and the mixture is stirred at a temperature of from about 0° C. or less up to the boiling point of the mixture, or higher. The reaction can be carried out at subatmospheric, atmospheric or superatmospheric pressure. The temperature and pressure are not critical.

Stirring is continued until the reaction is complete and this, as is obvious, will be dependent upon the specific reactants employed, reaction conditions used and the size of the batch. At completion of the reaction, one can, if so desired, separate the complex from the diluent using conventional procedures.

The structure of the formula A complex, identified herein as [A'] is believed to be (schematically) as follows:

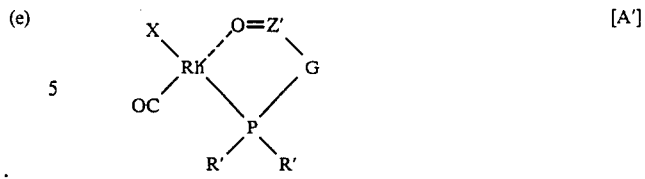 [A']

wherein R', G and X are as before and Z' is —P—R'R'; —COR" or —CR" and wherein R" is R'. The formula A complex may be formed in either the cis—or trans-geometrical isomer, wherein the X—and OC—moieties in complex A' are as they appear or are reversed.

Analysis to date of complex A' by NMR and IR has demonstrated the cis-isomer as the form present at room temperature.

In the catalytic reaction for the production of the carboxylic acids the catalyst complex can be prepared and then added to the reactor or it can be prepared in-situ during the reaction.

Carbon monoxide may be combined with Formula A complexes to form Formula B complexes. That complex may be represented, schematically by Formula B' as follows:

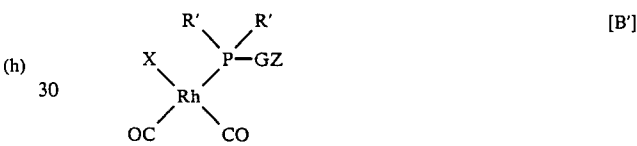 [B']

wherein X, R', G and Z are as before.

If desired, Formula B complexes may be prepared in advance of the process by the carbonylation of Formula A complexes or the like. Formula B complexes have not yet been isolated, but, from spectral analyses of the reaction mixture appear to have the indicated structure. Other procedures which will be apparent to those skilled in this art may also be utilized to make Formula B complexes.

The concentration of ligand charged to the catalytic reaction can be varied from a molar ratio of ligand to rhodium of from about 50:1 to 1:50, preferably from 10:1 to 1:10 and most preferably from about 3:1 to 1:1.

The reaction is carried out at mild reaction temperatures, from about 80° C. to 170° C., more preferably 100° C. to about 150° C.

The reaction pressure employed is milder than those generally employed. The pressure of the reaction generally is up to about 450 psig and preferably, from 50 psig to 350 psig, most preferably from 100 psig to 250 psig.

The reaction is carried out under carbon monoxide pressure to enhance catalyst stability. It should be understood that carbon monoxide is not consumed. Whatever carbon monoxide is employed in the reaction intermediates, is believed regenerated in a later step. Accordingly, there is no overall consumption of carbon monoxide and it can be regarded as an adjunct of the instant catalyst system.

One of the major problems associated with the prior art isomerizations of methyl formate to acetic acid is said to be the formation of methyl acetate by-product via esterification of product acetic acid or acetic acid solvent with methyl formate. The present process is highly selective, with over 95% of the product typically being the desired acid. Accordingly, the present process eliminates that defect found in prior isomerizations of formates to acids.

The reaction time varies depending upon the reaction parameters, reactor size and charge, and the individual components employed at the specific process conditions. The reaction can be a batch or continuous reaction.

In addition one can optionally have a solvent present. Many essentially inert solvents are known as useful, essentially inert, diluents and illustrative thereof one can mention 1,4-dioxane, the polyethylene glycols di-ethers or esters, diphenyl ether, sulfolane, toluene, carboxylic acids as well as any other diluent or solvent which does not interfere with the reaction to any significant extent. When a solvent is employed, the preferred one is acetic acid. Acetic acid is effective in preventing conversion rate decreases and catalyst precipitation during long term operations.

Preparation Example I

All experiments were carried out in 100 cc Fisher Porter ® glass pressure bottle equipped with a gas inlet line and various valves that permit addition of the reagents via a syringe needle. In a typical experiment a mixture of degassed methyl formate containing dissolved $Rh(CO)_2AcAc^{1/}$ and $R_2P(CH_2)_nP(O)R_2$ was added under CO to the pressure bottle containing LiI. $CH_3I$ was then added and the bottle was sealed by means of a valve and pressurized to 15 psig CO. The bottle was heated to the desired temperature by means of an oil bath. At the desired temperature the pressure was adjusted to the selected operating pressure by addition of CO. The reaction was carried out for 0.5 to 4.0 hours. After the allocated time period the pressure bottle was cooled and the product mixture was transferred to a chilled bottle under $N_2$. The liquid products were analyzed via a Varian 3700 gas chromatograph equipped with 30M Supelco DB 1701 capillary column or a HP-5880 gas chromatograph equipped with two $\frac{1}{8}'' \times 10'$ 60/80 mesh chromosorb 101 columns.
1/ AcAc is acetylacetonate Example 1

The reaction was carried out according to the procedure of Preparation Example 1 at several temperatures while maintaining a constant operating pressure of 150 psig. In each case the Fisher Porter ® bottle was charged with the following components (Ph=phenyl)

| $Rh(CO)_2AcAc$ | 0.12 g | (0.46 mm) |
| $Ph_2PCH_2CH_2P(O)Ph_2$ | 0.21 g | (0.5 mm) |
| LiI | 1.5 g | (11.0 mm) |
| $CH_3I$ | 2.0 ml | (31.6 mm) |
| Methyl Formate | 7.0 ml | |

The results are summarized in the following table:

| Run | Temp. °C. | Methyl Formate Conversion, % | Acetic Acid Rate, $Mhr^{-1}$ |
| --- | --- | --- | --- |
| 1 | 80 | 10 | 0.5 |
| 2 | 100 | 35 | 2.1 |
| 3 | 115 | 42 | 2.6 |

In all cases the selectivity to acetic acid is greater than 95%. Only trace amounts of methyl acetate, acetic anhydride and water were detected. These runs demonstrate that the reaction can be carried out at various temperatures. The temperature of 80° C. is seen to be the lowest temperature under these conditions providing significant product.

Example 2

In this example the use of acetic acid as a solvent is demonstrated. The pressure bottle was charged with the following components.

| $Rh(CO)_2AcAc$ | 0.12 g | (0.46 mm) |
| $Ph_2PCH_2CH_2P(O)Ph_2$ | 0.21 g | (0.5 mm) |
| LiI | 1.5 g | (11.0 mm) |
| $CH_3I$ | 2.0 ml | (31.6 mm) |
| Methyl Formate | 3.5 ml | |
| Acetic Acid | 3.5 ml | |

The reaction was carried out according to Example 1 at 115° C. and 150 psig (total operating pressure) for 2 hours. The methyl formate conversion was 63%. The acetic acid rate was 2.0 $Mhr^{-1}$ with a selectivity of 98%. Very small amounts of methyl acetate, acetic anhydride and water were detected. This example demonstrates that acetic acid will serve as a solvent for the reaction.

When other promoters are substituted for $CH_3I$, such as hydriodic acid, ethyl iodide, trimethyl ammonium iodide, methyl bromide, methyl triphenyl phosphonium chloride and the like, similar results are obtained.

Example 3

The pressure bottle was charged with the same amount of reagents as in Example 1 except that $CH_3I$ was not utilized. The reaction was carried out at 115° C. and 150 psi for 2.0 hours. The methyl formate conversion was 35%. The acetic acid rate was 2.7 $Mh^{-1}$ with a selectivity of 97%.

When other ligands such as

$Ph_2P(CH_2)_2COCH_2CH_3$;

$(CH_3)_2P(CH_2)_3P(O)(CH_3)_2$; $(Tolyl)_2P(CH_2)_2C(O)OCH_2CH_3$ and $(Benzyl)_2P(CH_2)_2P(O)(Benzyl)_2$ are substituted for the ligand of Example 3, similar results are obtained.

Example 4

The pressure bottle was charged with the following components.

| $Rh(CO)_2AcAc$ | 0.12 g | (0.46 mm) |
| $Ph_2PCH_2CH_2P(O)Ph_2$ | 0.21 g | (0.5 mm) |
| $SrI_2$ | 3.83 g | (11.2 mm) |
| Methyl Formate | 7.0 ml | |

The reaction was carried out at 100° C. and 150 psig total operating pressure for 2.0 hrs. The methyl formate conversion was 35%. The acetic acid rate was 2.85 $Mhr^{-1}$ and the selectivity was 98%. This run demonstrates that $SrI_2$ will serve as a metal halide for the isomerization reaction.

Example 5

The reaction was carried out exactly as Example 4 except that the reaction temperature was 80° C. The methyl formate conversion was 10%. The acetic acid rate was 0.8 $Mhr^{-1}$ and the selectivity was 96%.

Example 6

The following components were charged to the pressure bottle.

| | | |
|---|---|---|
| Rh(CO)₂AcAc | 0.12 g | (0.46 mm) |
| Ph₂PCH₂CH₂P(O)Ph₂ | 0.21 g | (0.5 mm) |
| LiI | 3.00 g | (22.3 mm) |
| Methyl Formate | 7.0 ml | |

The reaction was carried out according to Example 1 for 2.0 hours at 100° C. and 150 psi total operating pressure. The methyl formate conversion was 55%. The acetic acid rate was 4.5 Mhr$^{-1}$ and the selectivity was 98%.

Similar results are obtained when other rhodium sources are substituted; such as Rh₂(CO)₄Br₂, Rh(CO)₂AcAc, Rh₂(CO)₈, K₄Rh₂I₂(SnI₂)₄, and [(n-C₄H₉)₄N][Rh(CO)₂I₂].

Example 7

Preparation of Complexes

A series of runs was performed using the following general procedure to produce the complexes of formulas A' and B'.

A solution of 2.5 millimoles (mm) of C₆H₅PCH₂P(O)(C₆H₅)₂ in 10 ml methylene chloride was added to a solution of 1.25 mm [Rh(CO)₂Cl]₂ in 10 ml methylene chloride. The mixture was allowed to stir for 10 minutes and the methylene chloride was removed under vacuum. The residual viscous oil was redissolved in 10 ml methylene chloride and the solvent evaporated again. This procedure was repeated three to four times.

The residue from the final evacuation was dissolved in 5 ml methylene chloride. Yellow crystals precipitated upon standing. The crystals were filtered, washed with methylene chloride and dried under vacuum. X-ray crystallographic analysis showed that the compound corresponds to:

cis-RhCl(CO)[(C₆H₅)₂PCH₂P(O)(C₆H₅)₂]·CH₂Cl₂, which contains a Rh to O bond. The infrared spectrum displayed a single intense bond at 1990 cm$^{-1}$ due to the presence of coordinated CO to Rh in the complex.

The above procedure was followed exactly using (C₆H₅)₂P(CH₂)ₙP(O)(C₆H₅)₂; in which n was 2, 3 and 4 and for (C₆H₅)₂P(CH₂)ₙC(O)OC₂H₅ in which n was 2. In all instances yellow crystals were recovered which gave infrared spectra similar to the first complex described above, having an intense band at 1990 cm$^{-1}$ indicating the formation of the similar structure. The complex products produced had the formulas:

cis-RhCl(CO)[(C₆H₅)₂PC₂H₄P(O)(C₆H₅)₂]

cis-RhCl(CO)[(C₆H₅)₂PC₃H₆P(O)(C₆H₅)₂]

cis-RhCl(CO)[(C₆H₅)₂PC₄H₈P(O)(C₆H₅)₂]

-continued cis-RhCl(CO)[(C₆H₅)₂PC₂H₄(O)OC₂H₅]

The dicarbonyl compounds of the above were prepared by reacting a portion of each of the above monocarbonyl compounds, respectively under CO pressure. Infrared spectra showed the formation of the dicarbonyl compounds had been achieved by the presence of two intense bands, typically at 2090 cm$^{-1}$ and 2010 cm$^{-1}$.

I claim:

1. A process for the production of organic carboxylic acids of the formula RCOOH which comprises the catalytic reaction of organic formate esters of the formula HCOOR in contact with carbon monoxide and a homogeneous catalyst system consisting essentially of a rhodium metal atom component, a phosphorus containing ligand in which there is present at least one oxo oxygen atom attached to a phosphorus atom or a carbon atom to form a Z group and $$\begin{array}{ccc} P & \text{or} & C \\ \parallel & & \parallel \\ O & & O \end{array}$$

group and said Z group is located at least one carbon atom removed from the phosphorus atom of the molecules represented by the formulas:

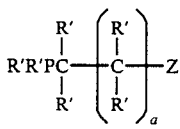
(V)

or

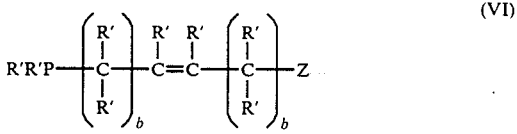
(VI)

and a halogen source; wherein R is an alkyl group having from 1 to 30 carbon atoms, or aryl or aralkyl groups having 6 to 10 ring carbon atoms with from 1 to 10 carbon atoms in the alk-moiety thereof, or alkenyl having from 2 to 30 carbon atoms; R' is H, aryl or aralkyl having from 6 to 10 ring carbon atoms and the alkyl moiety of said aralkyl group having 1 to 10 carbon atoms, or an alkyl group having from 1 to 10 carbon atoms; and wherein 1 or more of said R' groups can be substituted with a Z group but not more than 3 of said R' groups in the molecule are so substituted; a is an integer form 0-4; b is an integer from 0-3; and Z is a member selected from the group consisting of:

$$-PR'R'; \quad -C(O)OR'' \quad \text{or} \quad -CR'' $$
$$\parallel \qquad \qquad \qquad \qquad \parallel$$
$$O \qquad \qquad \qquad \qquad O$$

wherein R'' is R' or H and said reaction is carried out at a reaction temperature up to about 170° C. and a reaction pressure up to about 450 psig.

2. A process as claimed in claim 1 wherein the reaction temperature is from about 80° C. to 170° C.

3. A process as claimed in claim 1 wherein the reaction temperature is from about 100° C. to 150° C.

4. A process as claimed in claim 1 wherein the reaction pressure is from about 50 to 350 psig.

5. A process as claimed in claim 1 wherein Z is

6. A process as claimed in claim 1 wherein Z is —C(O)OR".

7. A process as claimed in claim 1 wherein Z is —C(O)R".

8. A process as claimed in claim 1 wherein the number of C atoms in the linear chain between the P atom and the Z group is from 2 to 4.

9. A process as claimed in claim 1 wherein the halogen source is lithium iodide.

10. A process as claimed in claim 9 wherein the mole ratio of LiI to Rh is from about 128:1 to 1:1.

11. A process as claimed in claim 1 wherein the halogen source is strontium iodide.

12. A process as claimed in claim 11 wherein the mole ratio of SrI to Rh is from about 128:1 to 1:1.

13. A process as claimed in claim 1 wherein the halogen source is a mixture of lithium iodide and methyl iodide.

14. A process as claimed in claim 13 wherein the mole ratio of LiI to $CH_3I$ is from about 10:1 to 1:10.

15. A process as claimed in claim 14 wherein the mole ratio of LiI to Rh is from about 128:1 to 1:1.

16. A process as claimed in claim 1 wherein HCOOR is methyl formate.

17. A process as claimed in claim 1 wherein R' is phenyl.

18. A process as claimed in claim 1 wherein the ligand is $Ph_2P(CH_2)_2 P(O)Ph_2$, wherein Ph is phenyl.

19. A process as claimed in claim 1 wherein the rhodium atom is supplied as a rhodium carbonyl compound.

* * * * *